(12) United States Patent
Ranganathan et al.

(10) Patent No.: US 6,863,924 B2
(45) Date of Patent: Mar. 8, 2005

(54) METHOD OF MAKING AN ABSORBENT COMPOSITE

(75) Inventors: Sridhar Ranganathan, Suwanee, GA (US); Jian Qin, Appleton, WI (US); Michael William Veith, Oshkosh, WI (US)

(73) Assignee: Kimberly-Clark WorldWide, Inc., Neenah, WI (US)

( * ) Notice: Subject to any disclaimer, the term of this patent is extended or adjusted under 35 U.S.C. 154(b) by 78 days.

(21) Appl. No.: 10/328,054

(22) Filed: Dec. 23, 2002

(65) Prior Publication Data

US 2004/0121905 A1 Jun. 24, 2004

(51) Int. Cl.[7] ................................ B05D 3/12
(52) U.S. Cl. ...................... 427/243; 427/244
(58) Field of Search ................ 427/243, 244, 427/245

(56) References Cited

U.S. PATENT DOCUMENTS

| | | |
|---|---|---|
| 3,338,992 A | 8/1967 | Kinney |
| 3,341,394 A | 9/1967 | Kinney |
| 3,471,598 A | 10/1969 | Battista |
| 3,502,538 A | 3/1970 | Petersen |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 3,890,254 A | 6/1975 | Guthrie |
| 3,902,497 A | 9/1975 | Casey |
| 3,997,647 A | 12/1976 | Lassen |
| 4,256,877 A | 3/1981 | Karlsson et al. |
| 4,340,563 A | 7/1982 | Appel et al. |
| 4,663,358 A | 5/1987 | Hyon et al. |
| 4,738,849 A | 4/1988 | Sawyer |
| 4,748,076 A | 5/1988 | Saotome |
| 4,795,668 A | 1/1989 | Krueger et al. |
| 4,888,238 A | 12/1989 | Katz et al. |
| 4,944,963 A | 7/1990 | Dabi et al. |
| 5,071,681 A | 12/1991 | Manning et al. |
| 5,108,820 A | 4/1992 | Kaneko et al. |
| 5,145,906 A | 9/1992 | Chambers et al. |
| 5,336,552 A | 8/1994 | Strack et al. |
| 5,362,761 A | 11/1994 | Uragami et al. |
| 5,372,877 A | * 12/1994 | Kannankeril ........... 428/311.71 |
| 5,409,703 A | 4/1995 | McAnalley et al. |
| 5,441,741 A | 8/1995 | Cheong |
| 5,454,801 A | 10/1995 | Lauritzen |
| 5,494,940 A | 2/1996 | Unger et al. |

(List continued on next page.)

FOREIGN PATENT DOCUMENTS

| | | |
|---|---|---|
| EP | 1164220 A1 | 6/2001 |
| JP | 11093073 A | 4/1999 |
| JP | 11347401 A | 12/1999 |
| WO | WO 99/01166 | 1/1999 |
| WO | WO 01/15649 A1 | 3/2001 |

OTHER PUBLICATIONS

Patent Abstract of Japan, No. 08176994 A, dated Jul. 9, 1996.

Primary Examiner—Erma Cameron
(74) Attorney, Agent, or Firm—Senniger Powers

(57) ABSTRACT

In a method of making an absorbent composite, a porous, stabilized structure is formed and impregnated with a flowable superabsorbent precursor. The flowable superabsorbent precursor is cross-linked to form a superabsorbent material within the stabilized structure. The surface area of one of the flowable superabsorbent precursor impregnated with the stabilized structure and the superabsorbent material formed within the structure is increased. In one embodiment, the surface is increased by freeze drying the impregnated structure.

55 Claims, 7 Drawing Sheets

U.S. PATENT DOCUMENTS

| | | | |
|---|---|---|---|
| 5,502,082 A | 3/1996 | Unger et al. | |
| 5,540,992 A | 7/1996 | Marcher et al. | |
| 5,541,234 A | 7/1996 | Unger et al. | |
| 5,567,478 A | 10/1996 | Houben et al. | |
| 5,573,994 A | 11/1996 | Kabra et al. | |
| 5,597,873 A | 1/1997 | Chambers et al. | |
| 5,651,862 A | 7/1997 | Anderson et al. | |
| 5,652,194 A | 7/1997 | Dyer et al. | |
| 5,728,085 A | 3/1998 | Widlund et al. | |
| 5,730,737 A | 3/1998 | Widlund et al. | |
| 5,795,439 A | 8/1998 | Eurípides et al. | |
| 5,814,034 A | 9/1998 | Widlund et al. | |
| 5,888,987 A | 3/1999 | Haynes et al. | |
| 5,948,829 A | 9/1999 | Wallajapet et al. | |
| 5,966,962 A | 10/1999 | Murray et al. | |
| 5,985,434 A | 11/1999 | Qin et al. | |
| 6,019,871 A | 2/2000 | Rökman et al. | |
| 6,027,795 A | 2/2000 | Kabra et al. | |
| 6,033,769 A | 3/2000 | Brueggemann et al. | |
| 6,203,845 B1 | 3/2001 | Qin et al. | |
| 6,251,479 B1 * | 6/2001 | Groitzsch et al. | 427/244 |
| 6,261,679 B1 * | 7/2001 | Chen et al. | 428/317.9 |
| 6,270,845 B1 | 8/2001 | Pappas et al. | |
| 6,309,454 B1 | 10/2001 | Harvey et al. | |
| 6,310,113 B1 | 10/2001 | Reichman et al. | |
| 6,369,293 B1 | 4/2002 | Reeves et al. | |
| 6,372,248 B1 | 4/2002 | Qin et al. | |
| 6,417,425 B1 | 7/2002 | Whitmore et al. | |
| 2001/0045177 A1 | 11/2001 | Harvey et al. | |

* cited by examiner

METHOD OF MAKING AN ABSORBENT COMPOSITE

BACKGROUND OF THE INVENTION

This invention generally relates to absorbent composites used in disposable articles such as diapers, child's training pants, feminine care articles, incontinence articles, bandages, and the like, and more particularly to such absorbent composites containing a superabsorbent material and methods for making such composites.

Conventional disposable articles typically include an absorbent composite, or absorbent core, conventionally formed by air forming, air laying or other forming technique. For example, the manufacture of such an absorbent composite may begin by fiberizing a fibrous sheet of cellulosic or other suitable material in a conventional fiberizer, or other shredding or comminuting device, to form discrete fibers. In addition, particles or fibers of superabsorbent material, which are water insoluble, water swellable and capable of absorbing up to at least about ten times their weight in 0.9% by weight concentration sodium chloride solution in water, are mixed with the discrete fibers. The fibers and superabsorbent particles are then entrained in an air stream and directed to a foraminous forming surface upon which the fibers and superabsorbent particles are deposited to form an absorbent fibrous web. In addition, bonding agents or other strengthening components may be incorporated to provide a more stabilized web.

Other techniques have also been employed to form absorbent composites. Such techniques have included dry-forming techniques, wet-forming techniques, and foam-forming techniques. The resulting absorbent composites have included absorbent fibers, natural fibers, synthetic fibers, foams, superabsorbent materials, binder materials, and strengthening components in desired combinations. However formed, the absorbent composite may then be stored or immediately directed for further processing (e.g., being cut into individual absorbent composites) and assembly with other components to produce a desired absorbent article.

While such absorbent composites incorporating particulate superabsorbent materials are useful, their absorptive properties may be limited due to the relatively low surface area to mass ratio of the particulate superabsorbent material within the composite. Also, the use of particulate superabsorbent materials is known to cause gel blocking, that is, as the superabsorbent particles swell upon absorbing liquid, it fills the voids within the composite and thereby blocks the flow of fluid within the composite to the superabsorbent particles upon further insults of the composite.

SUMMARY OF THE INVENTION

In general, one embodiment of a method of making an absorbent composite generally comprises forming a porous, stabilized structure and impregnating the structure with a flowable superabsorbent precursor. The flowable superabsorbent precursor is cross-linked to form a superabsorbent material within the stabilized structure. The surface area of one of the flowable superabsorbent precursor impregnated with the stabilized structure and the superabsorbent material formed within the structure, depending on when cross-linking occurs is increased.

In another embodiment, the method of forming an absorbent composite generally comprises forming a porous structure and impregnating the structure with a flowable superabsorbent precursor. The flowable superabsorbent precursor is cross-linked to form a superabsorbent material within the structure. The structure is freeze dried to increase the surface area of one of the flowable superabsorbent precursor impregnated within the structure and the superabsorbent material formed within the resilient structure, depending on when the cross-linking occurs.

One embodiment of a method of forming a superabsorbent material within a porous, stabilized structure generally comprises impregnating the structure with a flowable superabsorbent precursor. The flowable superabsorbent precursor is cross-linked to form a superabsorbent material within the stabilized structure. The surface area of one of the flowable superabsorbent precursor impregnated with the stabilized structure and the superabsorbent material formed within the structure, depending on when cross-linking occurs is increased.

Other features of the invention will be in part apparent and in part pointed out hereinafter.

Definitions

Within the context of this specification, each term or phrase below will include the following meaning or meanings:

"Bicomponent Fibers" refers to fibers that have been formed from at least two polymers extruded from separate extruders but spun together to form one fiber. Bicomponent fibers are also sometimes referred to as multicomponent or conjugate fibers. The polymers are usually, but not necessarily, different from each other. The polymers are arranged in substantially constantly positioned distinct zones across the length of the bicomponent fibers. The configuration of such a bicomponent fiber may be, for example, a sheath/core arrangement wherein one polymer is surrounded by another or may be a side-by-side arrangement, a pie arrangement or an "islands-in-the-sea" arrangement. Bicomponent fibers are taught in U.S. Pat. No. 5,108,820 to Kaneko et al.; U.S. Pat. No. 4,795,668 to Krueger et al.; U.S. Pat. No. 5,540,992 to Marcher et al.; and U.S. Pat. No. 5,336,552 to Strack et al.

"Bonded" refers to the joining, adhering, connecting, attaching, or the like, of at least two elements. Two elements will be considered to be bonded together when they are bonded directly to one another or indirectly to one another, such as when each is directly bonded to intermediate elements.

"Bonded-Carded" refers to webs that are made from fibers which are sent through a combing or carding unit, which separates or breaks apart and aligns the fibers in the machine direction to form a generally machine direction-oriented fibrous non-woven web. This material may be bonded together by methods that include point bonding, through air bonding, ultrasonic bonding, adhesive bonding or other suitable bonding technique.

"Foam" refers to a two-phase gas-solid system that has a supporting solid lattice of cell walls which are continuous throughout the structure. The gas (typically air) phase in a foam is usually distributed in void pockets called cells.

"Hydrophilic" describes a material or surface which is wetted by aqueous liquids in contact with therewith. The degree of wetting can, in turn, be described in terms of the contact angles and the surface tensions of the liquids and materials involved. Equipment and techniques suitable for measuring the wettability of particular materials or surfaces can be provided by a Cahn SFA-222 Surface Force Analyzer System, or a substantially equivalent system. When measured with this system, materials or surfaces having contact angles less than 90 degrees are designated "wettable" or hydrophilic, and those having contact angles greater than 90 degrees are designated "nonwettable" or hydrophobic.

"Meltblown" refers to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameters. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al, which is incorporated herein by reference. Meltblown fibers are microfibers which may be continuous or discontinuous, are generally about 0.6 denier or smaller, and are generally self bonding when deposited onto a collecting surface.

"Non-woven" refers to materials or structures that are formed without the aid of a textile weaving or knitting process. The structure comprises individual or groups of fibers or threads which are interlaid, but not in an identifiable manner as in a knitted fabric. Non-woven structures have been formed from many processes such as, for example, meltblowing processes, spunbonding processes, and bonded-carded processes.

"Open-cell foams" are polymeric materials having substantial void space in the form of cells defined by a plurality of mutually connected, three dimensionally branched webs of polymeric material, wherein the cells typically have openings to permit fluid communication from one cell to another. In other words, the individual cells of the foam are for the most part not completely discrete from each other. Thus, the cells in open-cell foams have intercellular openings, or "windows" which are large enough to permit fluid transfer from one cell to another within the foam structure. Sponge-like materials with interconnected cells are an example of open-cell foams.

"Spunbond" refers to small diameter fibers which are formed by extruding molten thermoplastic material as filaments from a plurality of fine capillaries of a spinneret having a circular or other configuration, with the diameter of the extruded filaments then being rapidly reduced by a conventional process such as that described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers of about 0.3 or larger, more particularly, between about 0.6 and about 10.

"Superabsorbent" refers to a water-swellable, water-insoluble organic or inorganic material capable, under the most favorable conditions, of absorbing at least about 10 times its weight and, more suitably, at least about 30 times its weight in an aqueous solution containing 0.9 weight percent sodium chloride in water.

"Surfactant" as used herein includes a single surfactant or a mixture of two or more surfactants. If a mixture of two or more surfactants is employed, the surfactants may be selected from the same or different classes, provided only that the surfactants present in the mixture are compatible with each other. In general, the surfactant can be any surfactant known to those having ordinary skill in the art, including anionic, cationic and nonionic surfactants. Examples of anionic surfactants include, among others, linear and branched-chain sodium alkybenzenesulfonates, alkyl sulfates, and alkyl ethoxy sulfates. Cationic surfactants include, for example, tallow trimethylammonium chloride. Examples of nonionic surfactants include, among others, alkyl polyethoxylates, polyethoxylated alkylphenols, fatty acid ethanol amides, and complex polymers of ethylene oxide, propylene oxide and alcohols.

"Thermoplastic" describes a material that softens when exposed to heat and which substantially returns to a non-softened condition when cooled to room temperature.

"Soluble" as used herein in reference to a material being water soluble or otherwise soluble in a particular solvent means that a material substantially dissolves in excess water or other solvent to form a solution, thereby losing its initial form and becoming essentially molecularly dispersed throughout the solution. As a general rule, a soluble material will be free from a substantial degree of cross-linking, as cross-linking tends to render a material water or otherwise solvent insoluble. A material that is insoluble is one that is not soluble as that term is defined herein.

DETAILED DESCRIPTION

Figure 1:
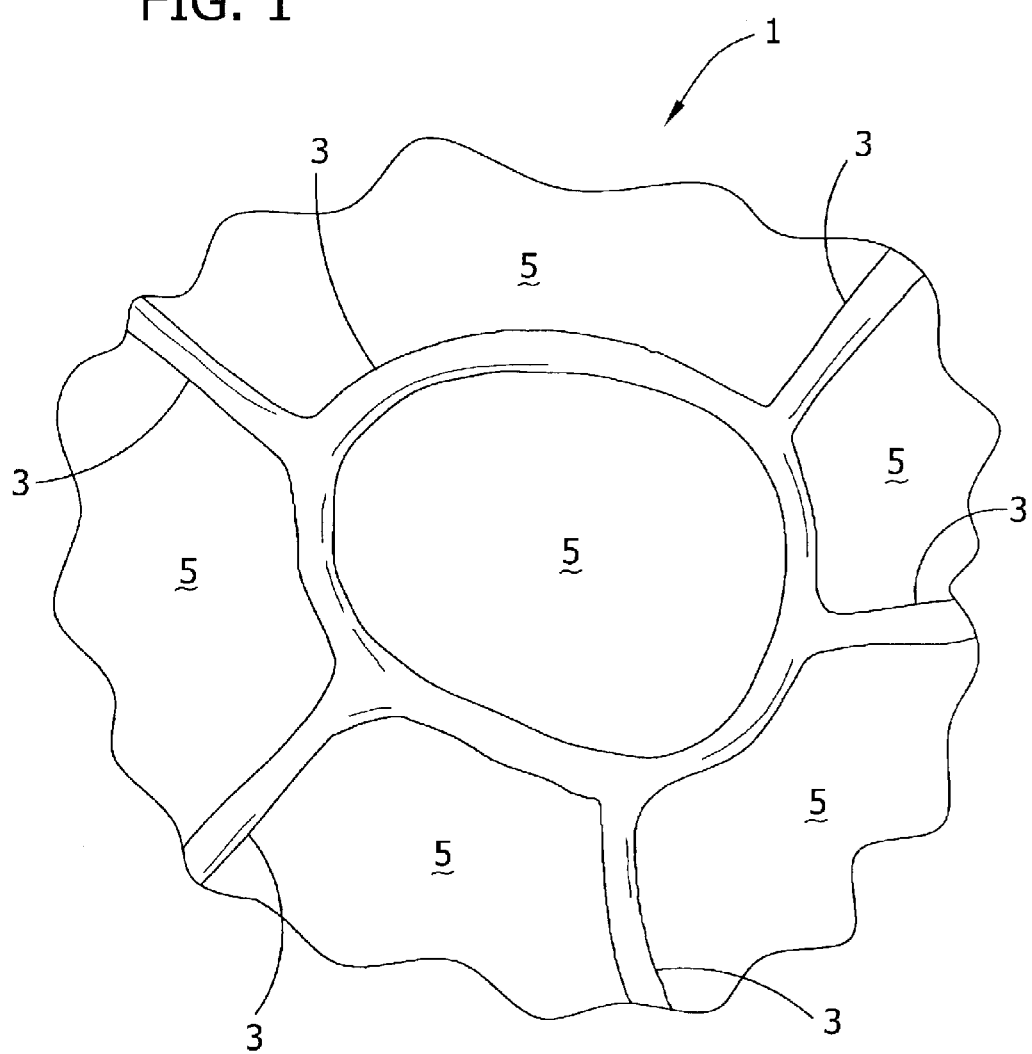
FIG. 1 depicts an element of a porous, stabilized structure, and more particularly an open cell foam structure, used in making one embodiment of an absorbent composite of the present invention.

The methods of the present invention can be configured to produce absorbent composites having a variety of uses. For example, possible uses include incorporation into a disposable article for absorbing various body exudates. Such articles are well known and can include, without limitation, feminine care pads, interlabial products, tampons, diapers, incontinence articles, training pants, bed pads, sweat absorbing pads, shoe pads, bandages, helmet liners, wipes, etc. As another example, the absorbent composite may be useful by itself, such as in the form of a tissue, towel, napkin or the like.

The absorbent composite formed in accordance with the methods of the present invention generally comprises a porous, stabilized structure and a superabsorbent material formed within the stabilized structure to have a high surface area exposed to body exudates taken into the composite upon subsequent insult thereof to facilitate absorption of the exudates by the superabsorbent material. In general, the absorbent composite is constructed by first forming the porous, stabilized structure and then impregnating all or part the structure with a flowable superabsorbent precursor capable of being cross-linked to form a suberabsorbent material within the structure as will be described in further detail later herein. Once the precursor is impregnated within the structure, additional operations are performed to cross-link the precursor to form a superabsorbent material within the structure and to increase the surface area of either the precursor or the absorbent material formed within the structure depending on when the cross-linking operation is performed. Increasing the surface area of the precursor and/or absorbent material within the structure thereby exposes more of the absorbent material of the formed composite to body exudates upon subsequent insult of the composite.

Suitable porous, stabilized structures for use in making the absorbent composite undergo minimal structural changes during the impregnation and subsequent processes they are subjected to. The structures are suitably insensitive to water (or other body exudates) and to the flowable absorbent precursor. The material (or materials) from which the structure is formed is suitably water-insoluble so that the microstructure of the material remains generally unchanged upon impregnating the structure with flowable superabsorbent precursor and upon subsequent insult of the absorbent composite by body exudates. The structure is also stabilized in that it suitably resists collapse upon wet loading, such as by the flowable superabsorbent material and by liquid body exudates taken into the absorbent composite, and even more suitably remains generally resilient during impregnation with the superabsorbent precursor and subsequent insults. The stabilized structure is suitably also resistant to expansion and internal restructuring, such as reorientation of fibers or cell walls within the structure, during impregnation and subsequent processing operations to form the superabsorbent material within the structure, as well as upon subsequent insult by body exudates.

Prior to being impregnated with the flowable superabsorbent precursor, the structure suitably has a high porosity, or low density, wherein the density of the structure is generally defined as (1−porosity)*density of the material used to form the structure. As an example, the structure prior to impregnation thereof suitably has a density of about 0.15 grams/cubic centimeter (g/cc) or less, more suitably about 0.12 g/cc or less, still more suitably about 0.08 g/cc or less and most suitably about 0.05 g/cc. The porosity of the structure prior to impregnation by the flowable absorbent precursor is suitably about 0.85 or greater, more suitably about 0.88 or greater, still more suitably about 0.92 or greater, and most suitably about 0.95.

The compressibility of the structure prior to impregnation thereof, as determined by measuring the compression of the structure at 0.9 psi, is in the range of about 2% to about 95%, more suitably in the range of about 3% to about 80%, and even more suitably in the range of about 5% to about 60%. The basis weight of the porous structure prior to being impregnated by the flowable superabsorbent precursor is suitably in the range of about 10 to about 400 grams/square meter (gsm), more suitably in the range of about 20 to about 200 gsm and most suitably in the range of about 50 to about 100 gsm.

In one embodiment the porous structure is a fibrous structure composed of synthetic fibers formed into a non-woven web in a conventional manner, such as by being air-formed, air-laid, bonded-carded or formed by other suitable techniques in which fibers are commingled to form a non-woven web or structure. As an example, one suitable carded fibrous structure can be formed to have a density of about 0.044 g/cc and a compression at 0.9 psi of about 77%. The fibrous structure may alternatively be a woven structure, such as for example, scrim material, and remain within the scope of this invention. The synthetic fibers are suitably polymeric, e.g., polyethylene, polypropylene or other suitable synthetic fiber, and may be formed by any of a variety of known techniques such as by being meltblown, spunbonded, extruded or formed by another suitable fiber forming technique.

The synthetic fibers may be either hydrophobic or hydrophilic. For example, synthetic fibers, which are typically initially hydrophobic upon forming thereof, may be rendered substantially hydrophilic through surface modification techniques that involve: 1) irradiating the surface of a polymeric material in the presence of oxygen to create active sites and then chemically grafting a polymer onto the active sites; 2) providing an organic surface coating by plasma discharge in the presence of a plasma polymerizable, halogenated hydrocarbon gas; 3) treating (e.g., oxidizing) the surface of the fibers so that it has a hydrophilic character with a high amount of cation-exchange groups; 4) applying corona discharge treatment, optionally with additional surfactant treatment; 5) depositing surfactants, proteins, polysaccharides or other hydrophilic materials by chemical precipitation, solution coating followed by evaporation of a solvent, supercritical fluid treatment to deposit solubolized hydrophilic agents; and/or other methods known in the art.

It is also contemplated that the fibers used to form the non-woven structure may be cellulosic, such as wood pulp fluff. In certain embodiments, the fibers may be suitably modified by surface or bulk treatments to maintain desirable properties of the structure.

The fibers of the structure are suitably bonded together so that the structure substantially resists expansion or other inter-fiber movement or reorientation during impregnation by the flowable absorbent precursor and upon further processing thereof. Bonding may be any commonly known bonding technique, such as by thermal bonding, ultrasonic bonding, point bonding, chemical bonding or other suitable bonding technique to bond the fibers together. It is also contemplated that a binder material or agent can be incorporated into the non-woven structure and is activatable such as by thermal activation, ultrasonic activation, chemical activation or other suitable means to melt and form inter-fiber bonds between the fibers of the structure. In one embodiment, the binder material comprises bicomponent (or multi-component) fibers in which at least one component of the fiber is melted or otherwise activated to bond with other fibers while at least one other component of the fiber is synthetic and remains unchanged in structure (e.g., remains resilient, non-absorbent and water-insoluble) following activation of the fibers.

In another embodiment, the porous structure comprises a resilient foam structure, and more suitably an open-celled foam structure. The foam structure may be constructed in accordance with any commonly known foam producing technique. For example, in one embodiment, the foam structure is a reticulated foam, and more suitably a melamine-formaldehyde foam. One suitable such foam is available from BASF of Charlotte, N.C. under the tradename BASOTECT®. This foam has a density of about 0.011 g/cc and a compression at 0.9 psi of about 10%. Another suitable reticulated foam is a reticulated polyurethane as disclosed in U.S. Pat. No. 3,890,254 the entire disclosure of which is incorporated herein to the extent it is consistent herewith. As another example, the foam structure may be that available from Rynel of Booth Bay, Me. under the tradename Rynel 562B, and has a density of about 0.107 g/cc and a compression at 0.9 psi of about 56%. FIG. 1 illustrates an element, generally indicated at 1 of a suitable foam structure, including the cell walls 3 and voids 5, for use in making an absorbent composite in accordance with one embodiment of the present invention.

In another embodiment, the porous structure is a low density foam structure made using a foam producing technology known as High-Internal-Phase-Ratio Emulsions (HIPE) technology and disclosed in U.S. Pat. No. 5,652,194 to Dyer et al, the entire disclosure of which is incorporated herein to the extent it is consistent herewith. HIPE technology generally involves polymerizing a particular type of water-in-oil emulsion. Such an emulsion is formed from a relatively small amount of a polymerizable monomer-containing oil phase and a relatively larger amount of a relatively monomer-free water phase. The relatively monomer-free, discontinuous "internal" water phase thus forms dispersed droplets surrounded by the continuous monomer-containing oil phase. Subsequent polymerization of the monomers in the oil phase forms a cellular foam structure. Aqueous liquid remaining in the foam structure after polymerization can be removed by pressing, thermal drying and/or vacuum dewatering. Polymeric foam structures, including foams prepared from water-in-oil emulsions, can be relatively closed-celled or, more suitably, relatively open-celled in structure.

Another suitable foam producing technique involves thermally induced phase separation (TIPS) of polymer solutions. In this technique, a polymer solution is quenched in order to induce phase separation, either through liquid-liquid phase separation or through polymer crystallization. When the TIPS technique results in forming a continuous polymer-rich phase, two additional processing steps can lead to producing a foam. First, the morphology of the phase-separated solution is preserved either through vitrification or crystallization of the polymer. This step preserves the small-scale morphology of the demixed solution. Next, the solvent is removed through freeze-drying or through supercritical extraction. The primary requirement for using the TIPS technique is polymer solubility. Low-density microcellular foams have been prepared with TIPS using many different polymers, including atactic polystyrene, isotactic polystyrene, poly(4-methyl-1-pentene), and polyacrylonitrile.

The flowable superabsorbent precursor generally comprises a cross-linkable material, such as one or more monomers and/or one or more non-cross-linked polymers capable of being cross-linked to form a water insoluble superabsorbent material. The term "polymer" as used in reference to the precursor includes, without limitation, homopolymers, copolymers such as, for example, block, graft, random and alternating copolymers, terpolymers, etc. and blends and modifications thereof. The term "polymer" also includes all possible geometrical configurations, including, without limitation, isotactic, syndiotactic and atactic tacticities.

The precursor also comprises a solvent, suitably in liquid form, capable of dissolving the monomer or non-cross-linked polymer to form a substantially uniformly dispersed precursor solution at the molecular level. For embodiments in which the flowable superabsorbent precursor is to be subsequently freeze dried as described later herein, the solvent used to prepare the precursor is suitably capable of first freezing and then undergoing sublimation wherein the solvent passes directly from its frozen state to a vapor state. As such, the solvent should have a freezing point at which the solvent changes from a liquid to a solid. As an example, in one desired embodiment the solvent is water and the monomer or non-cross-linked polymer is suitably water soluble. However, it is understood that other solvents may be used including, without limitation, alcohol, such as methanol, ethanol, isopropanol, glycerol and butyl alcohol, ketone, such as acetone and butanone, ether or a mixture of water and any of the above solvents, without departing from the scope of this invention as long as the monomer and/or non-cross-linked polymer is soluble in the solvent.

The precursor may also comprise a cross-linking agent, or cross-linker, which is soluble in the solvent being used, to facilitate subsequent cross-linking of the monomer and/or non-cross-linked polymer of the precursor to form a water-insoluble superabsorbent material within the structure. One suitable type of cross-linking agent, or cross-linker, includes latent cross-linkers which do not cross-link the non-cross-linked polymer when the solvent is present but will cross-link it after the superabsorbent material is formed, the solvent being significantly removed and an external treatment being applied, such as heating, microwaving, IR radiation, etc. Latent cross-linkers can be either polymerizable or non-polymerizable.

Polymerizable latent cross-linkers contain at least one functional group which is capable of forming bonds with the monomer, such as ethylenically unsaturated groups, and one functional group which is capable of reacting with carboxylic acid groups on the monomers, such as hydroxyl, amino, epoxy groups. Suitable polymerizable latent cross-linkers include, but are not limited to, amino propyl viny ether, ethylene glycol vinyl ether, ethylene glycol allyl ether, 2-hydroxy ethyl methacrylate, and a mixture of thereof.

Non-polymerizable latent cross-linkers do not contain ethylenically unsaturated groups which are reactive to the monomer but at least two functional groups which are reactive to the pendant functional groups of the monomers or non-cross-linked polymer to form inter-molecular bonds. The non-polymerizable latent cross-linkers include, but are not limited to, diols, polyols, diamines, polyamines. Examples include ethylene glycol, diethylene glycol, triethylene glycol, polyethylene glycol, polyvinyl alcohol, polyethylene oxide, glycerol, 1,3-proanediol, 1,4-butanediol, 1,5-pantanediol, 1,6-hexanediol, 1,8-octanediol, 1,1,1-trimethylolpropane, 1,4-butanediamine, 1,5-pantanediamine, 1,6-hexanediamine, diethylenetriamine, polypropylene oxide, polypropylene glycol, hydroxyl cellulose, methyl cellulose, ethyl cellulose, polyvinyl amine, chitosan, polyaspartic acid, polyethyleneimine, carboxymethyl cellulose, starch, and analogs and derivatives thereof. Polyvalent metal ions are also useful latent cross-linkers. Examples include $Al^{3+}$, $Zr^{4+}$, $Fe^{3+}$, $Ce^{3+}$, $Ce^{4+}$, $Ti^{3+}$, and $Cr^{3+}$.

Other suitable cross-linkers include reactive cross-linkers which form cross-linking points in the presence of solvent. This type of cross-linker is especially important when the cross-linking step is conducted prior to increasing the surface area of the precursor within the structure. The reactive cross-linkers can be either polymerizable or non-polymerizable. The functional groups capable of reacting pendant functional groups on the non-cross-linked polymer include, without limitation, diepoxy or polyepoxy compounds, dialdehydes or polyaldehydes. Examples include glycerin diglycidyl ether, polyethylene glycol diglycidyl ether, glutaraldehyde, and analogs and derivatives thereof. When a reactive cross-linker is used in a precursor comprising a monomer or monomers, suitable reactive cross-linkers include any compound comprising at least two ethylenically unsaturated functional groups. Examples include methylene bisacrylamide, and analogs and derivatives thereof.

Alternatively, self cross-linkable functional groups can be introduced onto the non-cross-linked polymer backbone through a chemical modification, such as grafting, and form cross-linking points between the functional groups when proper conditions are provided. For example, a non-cross-linked absorbent polymer is graft polymerized with an organic moiety capable of graft polymerization with the polymer which moiety contains a trialkoxy silane functional group or which moiety reacts with water to form a silanol group. The silanol groups between two polymer chains react each other to form cross-linking points. Ethylenically unsaturated momoners containing a trialkoxy silane functional group are particularly desired. A particularly desirable ethylenically unsaturated monomer containing a trialkoxy silane functional group is methacryloxypropyl trimethoxy silane, which is commercially available from Dow Corning, Midland, Mich., under the trade designation Z-6030 Silane. Other suitable ethylenically unsaturated monomers containing trimethoxy silane functional group include, without limitation, methacryloxyethyl trimethoxy silane, methacryloxypropyl triethoxy silane, methacryloxypropyl tripropoxy silane, acryloxypropylmethyl dimethoxy silane, 3-acryloxypropyl trimethoxy silane, 3-methacryloxypropylmethyl diethoxy silane, 3-methacryloxypropylmethyl dimethoxy silane, and 3-methacryloxypropyl tri(methoxyethoxy) silane.

The amount of cross-linking agent in the precursor suitably ranges from about 0.25% to about 15% by weight based on the dry weight of the superabsorbent precursor to be cross-linked. Higher amounts of cross-linking agent usually leads to higher cross-linking density and a lower molecular weight ($M_c$) between the cross-links. The amount of cross-linking agent is more suitably in the range of about 1% to about 8% by weight, and even more suitably about 1% to about 5% by weight. The concentration of the copolymer in the solvent, which in this embodiment is water, is suitably in the range of about 10% to about 60%, more suitably in the range of about 15% to about 50%.

The superabsorbent precursor may alternatively include hydrolyzed partially neutralized starch acrylonitrile graft copolymers, partially neutralized starch acrylic acid graft copolymers, partially neutralized saponified vinyl acetate-acrylester copolymers hydrolyzed acronitrile copolymers carboxymethyl cellulose, carboxymethyl starch, chitosan salts, partially neutralized polyaspartic acid, polyquartenary ammonium salts, polyvinyl amines, polyethylene imines, or combinations of any of these. As an example, one suitable precursor comprises carboxymethyl cellulose (CMC) having a degree of substitution (DS) ranging from about 0.3 to about 3, more suitably from about 0.4 to about 1.5, and even more suitably from about 0.5 to about 1.0, a molecular weight ranging from about 100,000 to about 10,000,000, more suitably from about 200,000 to about 1,000,000, and even more suitably from about 300,000 to about 1,000,000, and a viscosity at 1 wt. % aqueous solution at 25° C. ranging from about 10 to about 80,000 centipoises (mPa.s), more suitably from about 100 to about 50,000 centipoises, and even more suitably from about 500 to about 10,000 centipoises.

In another embodiment, the flowable superabsorbent precursor material comprises a linear neutralized polyacrylic acid. "Linear" means the polyacrylic acid precursor is substantially unbranched in structure. "Neutralized" means that the carboxyl acid groups of the precursor molecule are neutralized to their salt equivalents using a base such as sodium hydroxide, potassium hydroxide, ammonium hydroxide, sodium carbonate, or other hydroxides and basic salts. Suitable linear neutralized polyacrylic acid is about 40% to about 90% neutralized, more suitably about 45% to about 85% neutralized, and most suitably about 50% to about 80% neutralized.

The polyacrylic acid superabsorbent precursor can contain a linear polyacrylic acid with nonpolymerizable latent cross-linkers or a copolymer of acrylic acid and a polymerizable latent cross-linker such as aminopropyl vinyl ether or ethylene glycol vinyl ether. Other suitable cross-linking agents or cross-linkers include any of the cross-linkers described previously.

The flowable superabsorbent precursor can also comprise a mixture of two or more such precursors. Where two such precursors are combined to form the flowable superabsorbent precursor used to impregnate the porous, resilient structure, the ratio of one precursor to the other precursor can be between 99:1 to 1:99. Suitably the percentage of the first precursor is about 10% to about 90%, and more suitably about 30% to about 70%. The advantages of using two or more precursors in combination include providing complimentary absorbent properties, wettability, complementary liquid wicking properties, and other desirable properties.

The flowable superabsorbent precursor can be a solution of a monomer/monomers or a non-cross-linked polymer/polymers. In the case of a monomer solution, an initiator is required in order to trigger polymerization after the precursor solution is impregnated into a porous, stabilized structure to obtain a superabsorbent polymer from the monomer. The initiator may be any conventional polymerization initiator. The initiator is suitably substantially soluble in the solvent and is selected based, in part, on the intended method of inducing the reaction of the monomer. Thus, light and heat activated initiators are useful initiators. Optional polymerization initiators include free radical initiators including, for example, thermally instable compounds such as sodium, potassium, and ammonium persulfates, caprylyl peroxide, benzoyl peroxide, hydrogen peroxide, cumene hydroperoxides, tertiary butyl diperphthalate, tertiary butyl perbenzoate, sodium peracetate, sodium percarbonate, and the like.

Conventional redox initiator systems can also be used, e.g., systems combining the foregoing peroxygen compounds with reducing agents such as sodium bisulfite, L-ascorbic acid or ferrous salts. The amount of the initiator used may be that amount conventionally used in the polymer field. Typically, the initiator is used at a level of up to about 5 mole percent, suitably about 0.001 to about 0.5 mole percent, based on the total moles of polymerizable monomer. Certain external energy is needed to break down the initiator, such as heat, UV and microwave radiation.

The flowable superabsorbent precursor is suitably in the form of a liquid having a viscosity suitable for flowing within the porous, stabilized structure to substantially saturate all or one or more discrete regions of the structure. The viscosity of the precursor depends generally on the concentration of the monomer or non-cross-linked polymer in the precursor solvent. As an example, the viscosity of the precursor at 25° C. is suitably in the range of about 10 to about 80,000 centipoises, more suitably from about 100 to about 50,000 centipoises and even more suitably from about 500 to about 10,000 centipoises. It is contemplated that the flowable superabsorbent precursor may alternatively be in a form other than a liquid, such as in the form of a flowable gel or foam without departing from the scope of this invention.

Figure 2:
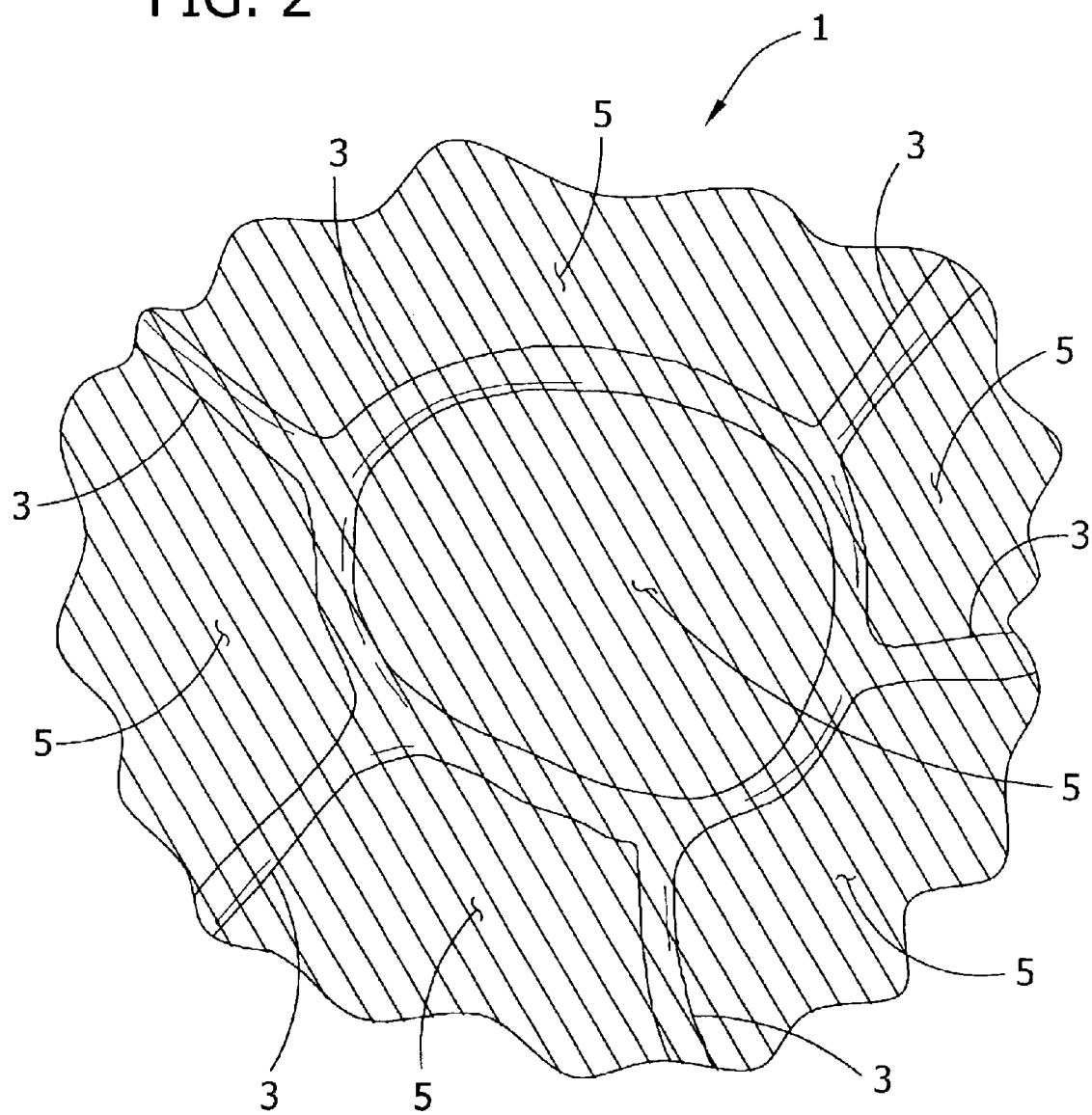
FIG. 2 is a schematic illustration of the element of FIG. 1 following impregnation of the stabilized structure with a flowable superabsorbent precursor.

In one embodiment, the flowable superabsorbent precursor is impregnated into the porous, stabilized structure by soaking the structure in a bath of the precursor. More particularly, the structure is soaked in such a bath for a sufficient duration, depending on the pore sizes of the structure and the viscosity of the precursor, to allow complete saturation of the structure by the precursor. It is also contemplated that only a portion, or discrete portions, of the structure may be soaked in the bath to provide one or more discrete, targeted regions of the structure which is impregnated with the precursor. FIG. 2 illustrates the stabilized structure element 1 of FIG. 1 following impregnation of the structure with the flowable superabsorbent precursor.

In another embodiment, the porous, stabilized structure is impregnated with the flowable superabsorbent precursor by printing the superabsorbent precursor onto the resilient structure and allowing the precursor to flow into the interior of the structure. A wide range of printing methods which are well known in the art, such as screen printing or the gravure printing process, are applicable for printing the flowable superabsorbent precursor onto the structure. In one embodiment, the flowable superabsorbent precursor is printed on the structure in a predetermined, desired configuration resulting in discrete regions of superabsorbent precursor on and within the resilient structure. The discrete regions of superabsorbent precursor may be formed in various locations and patterns within the structure according to the desired performance characteristics of the absorbent composite being formed. The discrete regions can be of any shape, such as, without limitation, circles, ovals, triangles, straight or curved bars, and rings.

In one embodiment, different shaped printing screens can be used to obtain different patterns or shapes of discrete regions of the structure impregnated with the precursor. To form such patterns or shapes of the discrete regions, a silkscreen tray is blocked or otherwise masked so that only an unblocked or unmasked portion of the screen defines the desired pattern and/or shape. A sufficient amount of the flowable superabsorbent precursor is delivered onto the screen and then spread with a roller or a soft rubber bladed squeegee. The unblocked portion of the screen thereby allows the flowable superabsorbent precursor to pass therethrough for printing the pattern and/or shape onto the structure. Depending on the duration and pressure of the printing operation, the precursor may fully or only partially impregnate the structure. The printing resolution of the superabsorbent precursor is generally a function of the viscosity of the precursor. For example, for the printing operation it is desired that the viscosity of the superabsorbent precursor be at least about 3000 to about 4000 centipoises or greater.

It is contemplated that the precursor can be impregnated into the porous, stabilized structure by other suitable techniques, such as by drawing the superabsorbent precursor into the structure using vacuum, or by gravity, without departing from the scope of this invention.

Once the precursor is impregnated within the structure, additional operations are performed on the structure, and more particularly to the precursor impregnated therein, to increase the surface area, and more particularly the porosity, of the precursor as described below and shown in FIGS. 3a, 3b and 3c. Alternatively, these operations may be performed after cross-linking the precursor as described later herein to increase the surface area of the absorbent material formed within the structure.

Figure 3A:
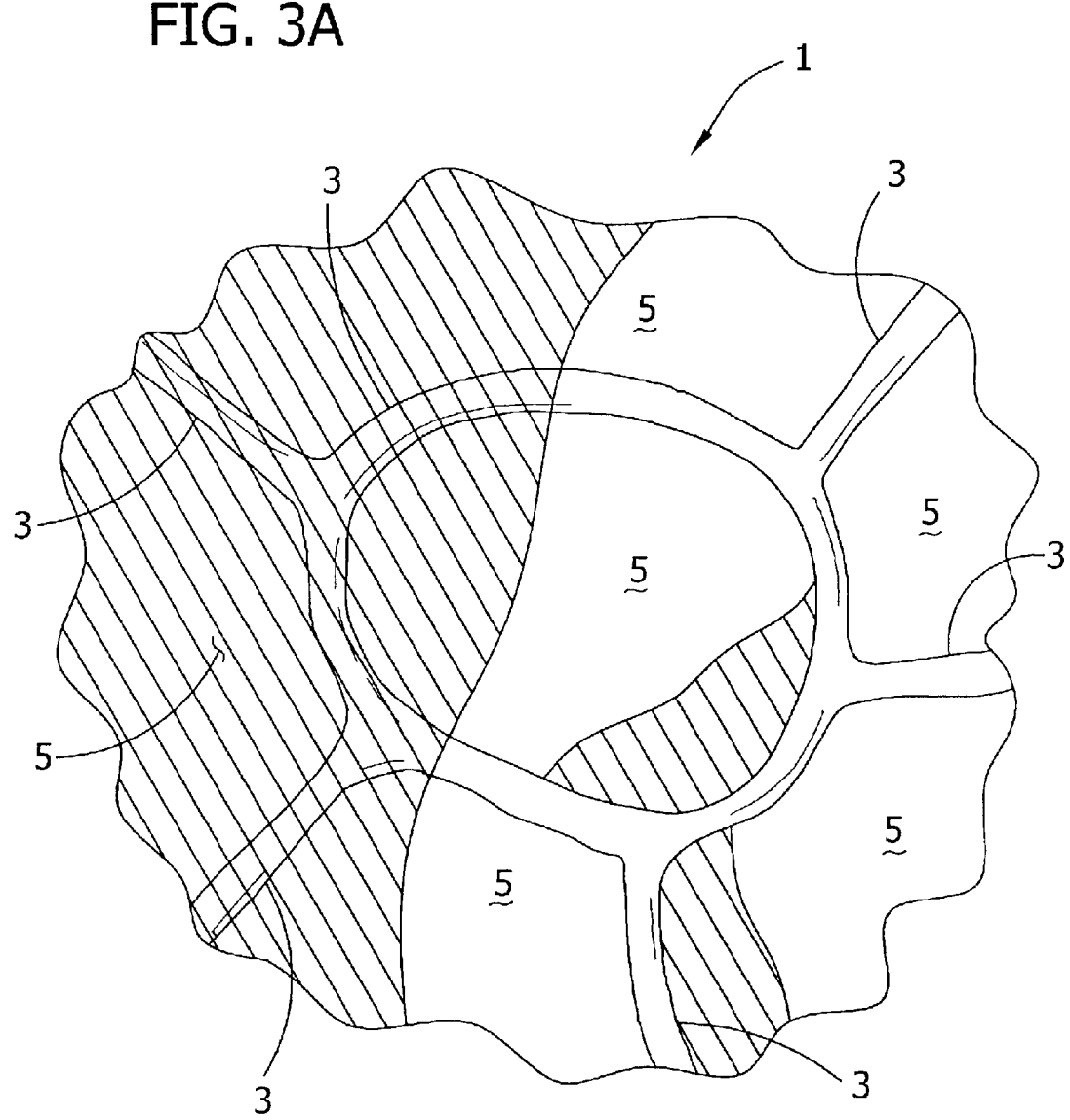
FIG. 3a is a schematic illustration of one embodiment of an absorbent composite of the present invention wherein the surface area of flowable superabsorbent precursor increased by freeze drying the impregnated stabilized structure.

In one embodiment, after the resilient structure is impregnated with the flowable superabsorbent precursor, the composite is freeze dried to increase the surface area of the precursor (and hence the surface area of the superabsorbent material formed from the precursor) within the structure as shown in FIG. 3a. That is, an increased surface area of the absorbent material formed in the structure is exposed to body exudates upon subsequent insult of the absorbent composite. As one example, U.S. Pat. No. 5,948,829 entitled Process for Preparing an Absorbent Foam issued to Wallajapet et al. on Sep. 7, 1999, the entire disclosure of which is incorporated herein by reference, discloses one manner in which the precursor may be freeze dried. The structure impregnated with the flowable superabsorbent precursor is subjected to cooling at temperature below the freezing point of the solvent of the precursor such that the precursor freezes and becomes a solid phase. With the monomer and/or non-cross-linked polymer (and the cross-linking agent if present) are essentially homogeneously dispersed in the flowable superabsorbent precursor mixture, the components of the precursor form an essentially continuous matrix within the frozen mixture when the precursor is frozen.

As will be recognized by one skilled in the art, the temperature to which the flowable superabsorbent precursor is cooled in order to freeze the precursor generally depends on the solvent, the monomer and/or the non-cross-linked polymer, the cross-linking agent if present, the initiator if present, and the relative concentrations of the respective components of the precursor. Where the solvent is water or at least an aqueous solution comprising water and other solvents wherein the solution is primarily water, it is generally desired that the temperature to which the precursor is eventually cooled be between about −50 degree C. and about 0 degree C., more suitably between about −50 degree C. and about −5 degree C., still more suitably between about −40 degree C. and about −10 degree C., and even more suitably between about −40 degree C. and about −20 degree C. In one particular embodiment in which water is the solvent and the non-cross-linked polymer is used in a concentration of between about 0.5 to about 2 weight percent, wherein the weight percent is based on the total weight of the solvent, it is suitable that the cooling rate used to freeze the solvent be about 0.4 degree C. per minute or less, more suitably it is about 0.3 degree C. per minute or less, and even more suitably it is about 0.1 degree C. per minute or less.

After the structure impregnated with the superabsorbent precursor has been cooled such that the precursor freezes and reaches a relatively stable temperature, the frozen solvent is substantially removed from the superabsorbent precursor to leave voids within the precursor which thereby increase the overall surface area of the precursor. For example, in one embodiment a suitable vacuum is used to sublime the frozen solvent from the precursor. As will be appreciated by one skilled in the art, the vacuum to be used for a particular frozen precursor generally depends on the solvent, the non-cross-linked polymer, the cross-linking agent if present, the relative concentrations of the respective components in the precursor and the temperature of the frozen precursor. Desirable vacuum pressures are suitably about 500 millitorrs or less, more suitably about 300 millitorrs or less, still more suitably about 200 millitorrs or less, and even more suitably about 100 millitorrs or less. In general, the higher the vacuum, the faster the rate of sublimation of the frozen solvent.

As used herein, sublimation of the frozen solvent from the precursor is meant to represent that substantially all of the solvent is removed from the precursor prior to any additional processing steps. It will be appreciated, however, that even after removal of substantially all of the solvent, a small amount of solvent may remain entrapped within the structure depending on the method and conditions under which the frozen solvent is sublimed. Generally, about 20 weight percent or less, more suitably about 15 weight percent or less, and even more suitably about 10 weight percent or less of the original amount of solvent in the precursor remains entrapped within the structure following sublimation.

Figure 3B:
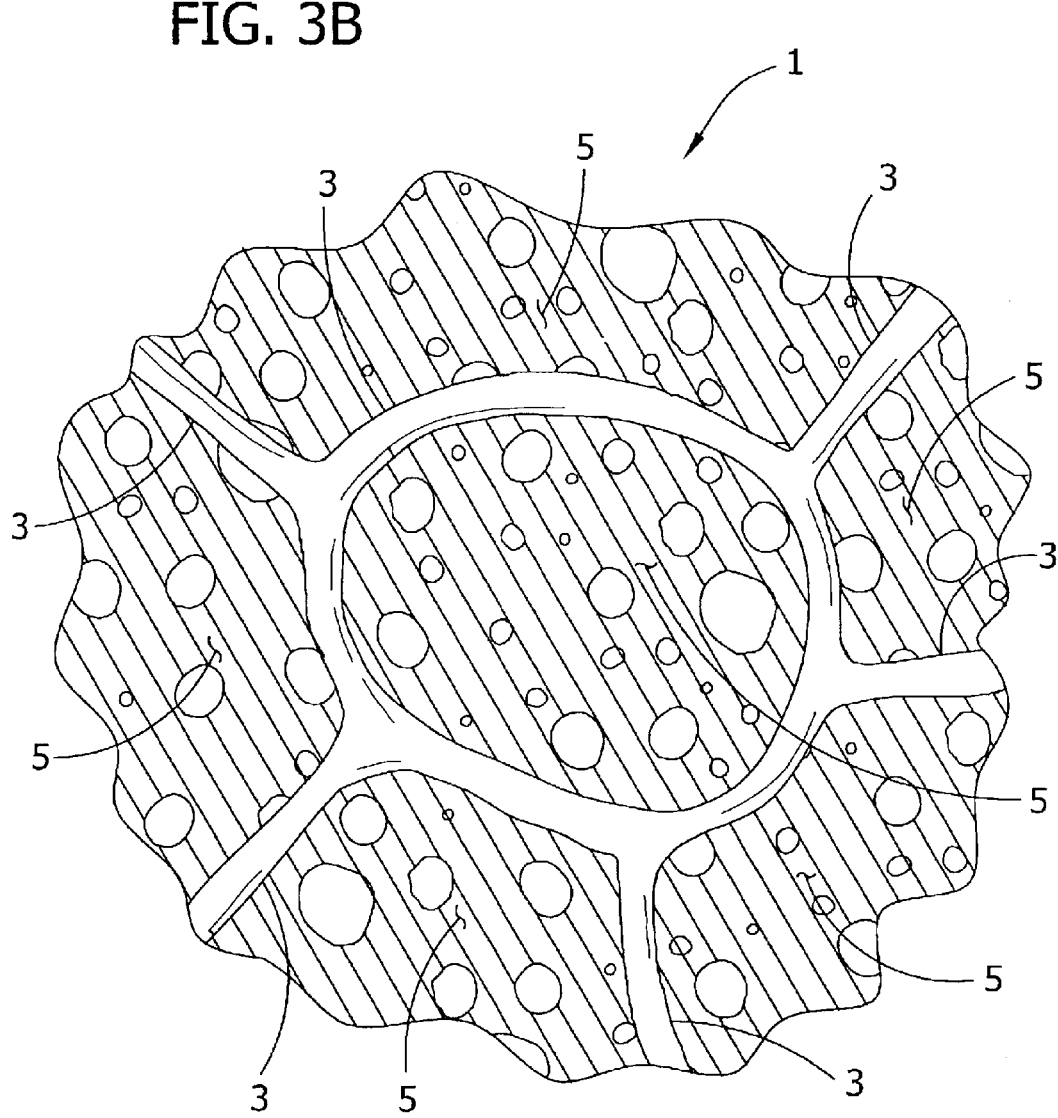
FIG. 3b is a schematic illustration similar to FIG. 3a but with the surface area of the flowable superabsorbent precursor increased instead by foaming the precursor within the stabilized structure.
Figure 3C:
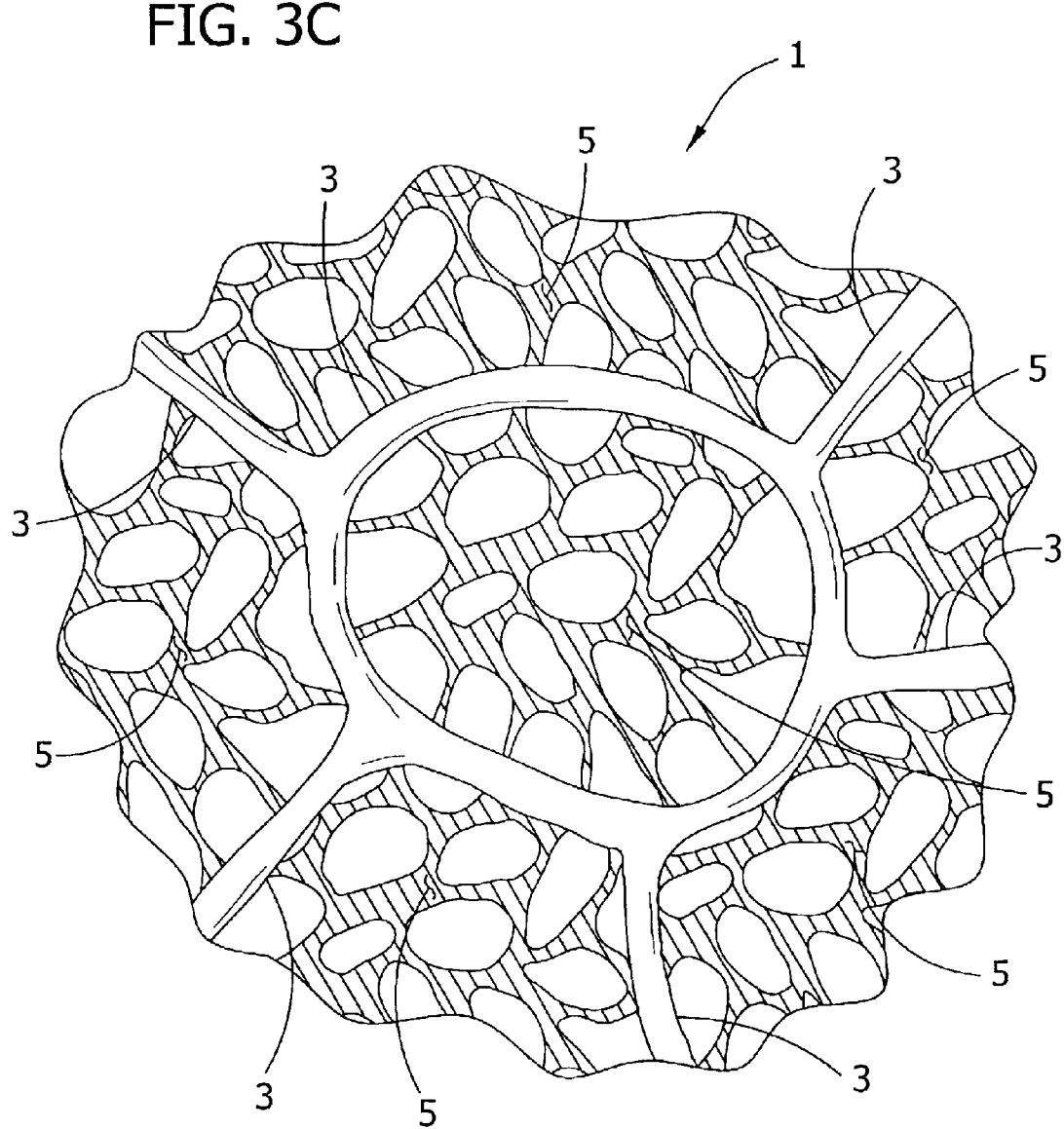
FIG. 3c is a schematic illustration similar to FIG. 3b but with larger voids formed in the flowable superabsorbent precursor following foaming of the precursor.

In another embodiment, after the porous, stabilized structure is impregnated with the flowable superabsorbent precursor, the precursor is foamed to increase the surface area of the precursor as shown in FIGS. 3b and 3c. For example, in a particular embodiment the structure impregnated with the superabsorbent precursor is subjected to wave energy which agitates and thereby foams the precursor. More particularly, a source of sonication energy applies ultrasound and/or audible waves of a desired wavelength, amplitude and shape to the superabsorbent precursor in the structure. As an example, U.S. Pat. No. 6,310.113 entitled Apparatus and Methods for Producing Superabsorbent Foams issued to Reichman et al. on Oct. 30, 2001, the entire disclosure of which is incorporated herein by reference, discloses one suitable manner in which mechanical waves can be applied to the precursor within the structure. Additionally, a blowing agent, which is suitably a suitable inorganic gas such as, air, nitrogen or carbon dioxide, or an organic gas or volatile liquid, may be introduced into the structure for foaming the precursor. The blowing agent causes multiple disruptions of the cell walls and formation of an extensively branched porous system in the foamed precursor which leads to increased surface area thereof.

Phase separation is another suitable technique for foaming the flowable absorbent precursor. As an example, U.S. Pat. No. 6,027,795 entitled Superabsorbent Foams and Method for Producing the Same issued to Kabra et al. on Feb. 22, 2000, the entire disclosure of which is incorporated herein by reference, discloses one manner in which phase separation is conducted. The flowable superabsorbent precursor is induced to phase separate into polymer concentrated and polymer dilute phases by quickly changing the precursor temperature within the structure, thereby resulting in interconnected polymer concentrated and polymer dilute phases. For example, phase separation can usually be induced by increasing the temperature of the precursor to a point above the lower consolute solution temperature (LCST), as will be understood by one skilled in the art. Some polymer/solvent solutions (particularly where the solvent is non-aqueous) exhibit an upper consolute solution temperature (UCST), and thus in these systems phase separation is induced by decreasing the temperature to a point below the UCST. In addition, the LCST or UCST can be modified when needed by the addition of other solutes or solvents (otherwise sometimes referred to as "phase separation enhancers").

Phase separation can also be induced by a number of other methods, such as by moving the precursor from a thermodynamically stable phase to a thermodynamically unstable condition. One skilled in the art can quite readily accomplish the phase separation merely by employing the polymer/solvent phase diagram for the particular polymer/solvent solution (e.g., the precursor) employed. In addition to inducing phase separation by raising or lowering the temperature, the addition of a phase separation enhancer (with or without a change in temperature) may also induce phase separation. Suitable phase separation enhancers include, without limitation, solutes such as salts, other solvents, and additional polymer of the type used in the precursor.

If a solvent phase separation enhancer employed is a non-solvent for the polymer but is miscible with the solvent of the homogeneous polymer/solvent solution, phase separation can be induced by spreading the enhancer over the surface of the polymer/solvent solution to form sheets or by dispersing the polymer/solvent solution in the enhancer to form particles. The phase separation enhancer can be mixed with the polymer/solvent solution in order to induce phase separation. The use of a phase separation enhancer may also be combined with a change in precursor temperature in order to induce phase separation, particularly when the phase separation enhancer is additional polymer.

With the flowable superabsorbent precursor impregnated within the porous, stabilized structure, the precursor is cured or otherwise cross-linked to form a water insoluble superabsorbent material within the structure. More particularly, the monomer and/or non-cross-linked polymer of the precursor is polymerized and/or cross-linked to form the superabsorbent material. As an example, the precursor may be cured in any conventional manner such as by subjecting the structure impregnated with the precursor to heat, microwaves, ultraviolet radiation, electron beam radiation and/or other suitable curing technique.

In one embodiment, cross-linking of the precursor suitably occurs after increasing the surface area of the precursor as described previously. For example, where the flowable superabsorbent precursor is freeze dried, cross-linking suitably occurs after the freeze-drying operation, particularly after sublimation of the solvent. In another embodiment, cross-linking suitably occurs prior to the surface area increasing operation. More particularly, in such an embodiment the cross-linking operation is performed to form the superabsorbent material within the structure and the structure is then subjected to a surface area increasing operation as described previously to increase the surface area of the superabsorbent material within the structure. For example, cross-linking of the flowable superabsorbent precursor may occur prior to the foaming operation. Alternatively, cross-linking may occur after the foaming operation without departing from the scope of this invention.

Following cross-linking, the structure can be subjected to a non-compressive drying operation to remove additional solvent from the superabsorbent material within the structure. Commonly known non-compressive drying techniques include, without limitation, freeze drying, through-air drying, air jet impingement drying, non-contact drying such as air flotation drying, through flow or impingement of superheated steam, microwave drying and other radiofrequency or dielectric drying, extraction by supercritical fluids, extraction by nonaqueous, lower surface tension fluids, infrared drying and other suitable drying techniques. Drying of the structure is particularly desirable where the surface area of the precursor is increased by foaming instead of by freeze drying (e.g., since freeze drying already removes most of the solvent)

EXAMPLE

Absorbent composites were formed from foam structures available from BASF of Charlotte, N.C. under the tradename BASOTECT. Each foam structure had a thickness of about 5 mm, a density of about 0.011 g/cc and a compression at 0.9 psi of about 10%. A flowable superabsorbent precursor was fully impregnated into each structure by soaking the structures in a bath of the precursor at certain concentration for at least 1 hour with gentle squeeze several times. The precursor comprised a solution of carboxymethyl cellulose (CMC), available from Hercules Inc. under the designation of cellulose Gum CMC-7H, sodium polyacrylate, available from Aldrich, having a molecular weight of 450,000, a degree of neutralization of about 70% and containing 2% hydroxypropyl cellulose as a latent cross-linker, available from Hercules Inc. under the designation of Klucel-M, or fully neutralized isobutylene-maleic anhydride copolymer sodium salt, available from Kuraray America, Inc., under the trade designation of ISOBAM-18, having a molecular weight of about 160,000 to about 170,000 and containing 4% diethylenetriamine as a latent cross-linker, all three polymers in non-cross-linked form dissolved in water.

Figure 4:
FIG. 4 is a photograph of a cross-section of one embodiment of an absorbent composite formed in accordance with the present invention.
Figure 5:
FIG. 5 is a magnified photograph of the cross-section shown in the photograph of FIG. 4.

The impregnated structures having different types and amount of precursor solutions were placed into separate stainless steel pans with a size of 10×20×1 inches. The pans were placed into a VirTis Genesis freeze dryer, Model 25 EL from The VirTis, Inc., and the temperature of the impregnated structures were slowly cooled down to about −50° C. at a rate of 0.3° C./minute. After an hour the condenser of the dryer was turned on and when the temperature of the condenser reached −70° C. the vacuum pump was switched on. Vacuum reading of the dryer has to be below 100 millitorrs after about 10 minutes to ensure an effective drying rate. It took about at least 15 hours to completely dry the samples. The samples obtained after freeze drying were heated at a different temperature for a different amount of time to cross-link the precursor polymers. Table 1 summarizes the samples. FIGS. 4 and 5 are magnified views of the interior of one of the samples showing the thin cell walls and sheets of superabsorbent material indicative of the freeze drying operation to increase the surface area of the precursor.

TABLE 1

| Sample No | Structure | Precursor | Crosslinker | Curing | Precursor in Foam |
|---|---|---|---|---|---|
| 1 | BASOTECT Foam | 1.5% CMC-7H | NA | 130° C./ 2 hours | 50% CMC |
| 2 | BASOTECT Foam | 1% CMC-7H | NA | 130° C./ 2 hours | 30% CMC |
| 3 | BASOTECT Foam | 0.5% CMC-7H | NA | 130° C./ 2 hours | 15% CMC |
| 4 | BASOTECT Foam | 2% Na-polyacrylate | 2% Klucel-M | 200° C./ 5 hours | 50% Na—PAA |
| 5 | BASOTECT Foam | 10% ISOBAM-18 | 4% Diethylene triamine | 150° C./ 2 hours | 70% ISOBAM-18 |

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. For example, features described in relation to one embodiment may be incorporated into any other embodiment of the invention.

Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description shall be interpreted as illustrative and not in a limiting sense.

What is claimed is:

1. A method of making an absorbent composite, said method comprising:

forming a porous, stabilized structure;

impregnating said structure with a flowable superabsorbent precursor comprising a solvent and a monomer;

polymerizing said monomer after impregnating said structure;

cross-linking said flowable superabsorbent precursor to form a superabsorbent material within the stabilized structure; and increasing a surface area of one of the flowable superabsorbent precursor impregnated within the stabilized structure and the superabsorbent material formed within the stabilized structure.

2. A method as set forth in claim 1 wherein the solvent is water.

3. A method as set forth in claim 1 wherein the flowable superabsorbent precursor has a viscosity in the range of about 10 and about 80,000 centipoises during the step of impregnating the structure with the flowable superabsorbent precursor.

4. A method as set forth in claim 1 wherein the step of increasing the surface area comprises freeze drying the stabilized structure after impregnating the structure with the flowable superabsorbent precursor.

5. A method as set forth in claim 4 wherein the step of freeze drying the structure is performed prior to the step of cross-linking the flowable superabsorbent precursor impregnated within the structure.

6. A method as set forth in claim 4 where the step of freeze drying the structure is performed subsequent to the step of cross-linking the flowable superabsorbent precursor impregnated within the structure.

7. A method as set forth in claim 4 wherein the step of freeze drying the structure comprises cooling the structure to a temperature between about −50 degrees Celsius and about 0 degrees Celsius at a cooling rate of about 0.4 degrees Celsius per minute or less.

8. A method as set forth in claim 1 wherein the step of increasing the surface area comprises foaming said one of the flowable superabsorbent precursor impregnated within the structure and the superabsorbent material formed therein.

9. A method as set forth in claim 8 wherein the step of increasing the surface area is performed prior to cross-linking the flowable superabsorbent precursor.

10. A method as set forth in claim 8 wherein step of increasing the surface area is performed subsequent to cross-linking the flowable superabsorbent precursor.

11. A method as set forth in claim 8 further comprising the step of removing the solvent from said one of the precursor and the superabsorbent material.

12. A method as set forth in claim 11 wherein said removing step comprises subjecting the structure to heat to thereby evaporate the solvent.

13. A method as set forth in claim 8 wherein said foaming step comprises agitating said one of the precursor and the superabsorbent material within the structure.

14. A method as set forth in claim 13 wherein said agitating step comprises subjecting the structure to wave energy.

15. A method as set forth in claim 13 wherein said agitating step comprises directing a blowing agent to flow through the structure.

16. A method as set forth in claim 8 wherein said foaming step comprises subjecting the structure to a phase separation process.

17. A method as set forth in claim 1 wherein the stabilized structure is formed to have a porosity of about 0.85 or greater prior to being impregnated with the flowable superabsorbent precursor.

18. A method as set forth in claim 17 wherein the stabilized structure is formed to have a porosity of about 0.95 or greater prior to being impregnated with the flowable superabsorbent precursor.

19. A method as set forth in claim 1 wherein the stabilized structure is formed to a have a density of about 0.15 g/cc or less prior to being impregnated with the flowable superabsorbent precursor.

20. A method as set forth in claim 19 wherein the stabilized structure is formed to a have a density of about 0.05 g/cc or less prior to being impregnated with the flowable superabsorbent precursor.

21. A method as set forth in claim 1 wherein the step of forming a stabilized structure comprises forming a foam structure.

22. A method as set forth in claim 1 wherein the step of forming a stabilized structure comprises forming a fibrous structure.

23. A method as set forth in claim 22 wherein the step of forming a stabilized structure comprises forming a fibrous structure wherein the position and orientation of fibers within the structure remains substantially constant during the steps of impregnating the structure with the precursor, cross-linking said precursor and increasing the surface area of said one of the flowable superabsorbent precursor impregnated within the structure and the superabsorbent material formed within said structure.

24. A method as set forth in claim 22 wherein the step of forming a stabilized structure comprises forming a fibrous structure comprising non-absorbent fibers and forming inter-fiber bonds between the fibers.

25. A method as set forth in claim 4 wherein the step of increasing the surface area of the flowable superabsorbent precursor further comprises subjecting the structure to a vacuum of about 500 millitorrs or less to facilitate removal of said solvent.

26. A method as set forth in claim 25 wherein about 20 weight percent or less of the solvent remains in the structure following the step of removing said solvent.

27. A method as set forth in claim 1 wherein said monomer is water-soluble.

28. A method as set forth in claim 1 wherein the impregnating step comprises soaking at least a portion of the stabilized structure in a bath of flowable superabsorbent precursor.

29. A method as set forth in claim 28 wherein the stabilized structure is soaked in said bath of flowable superabsorbent precursor until the entire structure is fully impregnated with said precursor.

30. A method as set forth in claim 1 wherein the impregnating step comprises printing the flowable superabsorbent precursor onto the stabilized structure.

31. A method as set forth in claim 1 wherein the step of cross-linking the superabsorbent precursor comprises subjecting said structure to at least one of heat, ultraviolet radiation and electron beam radiation.

32. A method as set forth in claim 1 wherein the step of increasing the surface area comprises increasing the porosity of said one of the flowable superabsorbent precursor impregnated within the stabilized structure and the superabsorbent material formed within the stabilized structure.

33. A method as set forth in claim 1 wherein the flowable superabsorbent precursor further comprises an initiator.

34. An absorbent composite made in accordance with the method as set forth in claim 1.

35. An absorbent article comprising the absorbent composite set forth in claim 34.

36. A method of forming a superabsorbent material within a porous, stabilized structure, said method comprising:
  impregnating said structure with a flowable superabsorbent precursor comprising a solvent and a monomer;
  polymerizing said monomer after impregnating said structure;
  cross-linking said flowable superabsorbent precursor to form a superabsorbent material within the stabilized structure; and
  increasing a surface area of one of the flowable superabsorbent precursor impregnated within the stabilized structure and the superabsorbent material formed within the stabilized structure.

37. A method as set forth in claim 36 wherein the flowable superabsorbent precursor has a viscosity in the range of about 10 and about 80,000 centipoises during the step of impregnating the structure with the flowable superabsorbent precursor.

38. A method as set forth in claim 36 wherein the step of increasing the surface area comprises freeze drying the stabilized structure after impregnating the structure with the flowable superabsorbent precursor.

39. A method as set forth in claim 38 wherein the step of freeze drying the structure is performed prior to the step of cross-linking the flowable superabsorbent precursor impregnated within the structure.

40. A method as set forth in claim 38 wherein the step of freeze drying the structure is performed subsequent to the step of cross-linking the flowable superabsorbent precursor impregnated within the structure.

41. A method as set forth in claim 36 wherein the step of increasing the surface area comprises foaming said one of the flowable superabsorbent precursor impregnated within the structure and the superabsorbent material formed therein.

42. A method as set forth in claim 41 wherein the step of increasing the surface area is performed prior to cross-linking the flowable superabsorbent precursor.

43. A method as set forth in claim 41 wherein the step of increasing the surface area is performed subsequent to cross-linking the flowable superabsorbent precursor.

44. A method as set forth in claim 36 wherein said monomer is water-soluble.

45. A method as set forth in claim 36 wherein the impregnating step comprises soaking at least a portion of the stabilized structure in a bath of flowable superabsorbent precursor.

46. A method as set forth in claim 45 wherein the stabilized structure is soaked in said bath of flowable superabsorbent precursor until the entire structure is fully impregnated with said precursor.

47. A method as set forth in claim 36 wherein the impregnating step comprises printing the flowable superabsorbent precursor onto at least one region of the stabilized structure.

48. A method as set forth in claim 47 wherein the impregnating step comprises printing the flowable superabsorbent precursor onto at least two discrete regions of the stabilized structure.

49. A method as set forth in claim 36 wherein the step of cross-linking the superabsorbent precursor comprises subjecting said structure to at least one of heat, ultraviolet radiation and electron beam radiation.

50. A method as set forth in claim 36 wherein the step of increasing the surface area comprises increasing the porosity of said one of the flowable superabsorbent precursor impregnated within the stabilized structure and the superabsorbent material formed within the stabilized structure.

51. A method as set forth in claim 36 wherein the flowable superabsorbent precursor further comprises an initiator.

52. An absorbent composite comprising a stabilized structure and a superabsorbent material formed therein in accordance with the method as set forth in claim 36.

53. An absorbent article comprising the absorbent composite set forth in claim 52.

54. A method of making an absorbent composite, said method comprising:

forming a porous, stabilized structure;

impregnating said structure with a flowable superabsorbent precursor;

cross-linking said flowable superabsorbent precursor to form a superabsorbent material within the stabilized structure; and increasing a surface area of one of the flowable superabsorbent precursor impregnated within the stabilized structure and the superabsorbent material formed within the stabilized structure by agitating said one of the flowable superabsorbent precursor and the superabsorbent material.

55. A method of making an absorbent composite, said method comprising;

forming a porous, stabilized foam structure;

impregnating said structure with a flowable superabsorbent precursor;

cross-linking said flowable superabsorbent precursor to form a superabsorbent material within the stabilized structure; and increasing a surface area of one of the flowable superabsorbent precursor impregnated within the stabilized structure and the superabsorbent material formed within the stabilized structure.

* * * * *